(12) United States Patent
Ni et al.

(10) Patent No.: US 7,071,312 B2
(45) Date of Patent: *Jul. 4, 2006

(54) EPIDERMAL DIFFERENTIATION FACTOR

(75) Inventors: Jian Ni, Germantown, MD (US); Ping Feng, Germantown, MD (US); Patrick J. Dillon, Carlsbad, CA (US); Reiner L. Gentz, Belo Horizonte-Mg (BR); Joseph Merregaert, Antwerp (BE); Patrick Smits, Herenthout (BE)

(73) Assignees: The University of Antwerp, Wilrijk (BE); Human Genome Sciences, Inc., Rockville, MD (US)

( * ) Notice: Subject to any disclaimer, the term of this patent is extended or adjusted under 35 U.S.C. 154(b) by 116 days.

This patent is subject to a terminal disclaimer.

(21) Appl. No.: 10/915,596

(22) Filed: Aug. 11, 2004

(65) Prior Publication Data

US 2005/0009141 A1    Jan. 13, 2005

Related U.S. Application Data

(60) Continuation of application No. 10/192,634, filed on Jul. 11, 2002, now abandoned, which is a continuation of application No. 09/317,850, filed on May 25, 1999, now abandoned, which is a division of application No. 08/815,718, filed on Mar. 12, 1997, now Pat. No. 5,981,220.

(60) Provisional application No. 60/014,220, filed on Mar. 27, 1996.

(51) Int. Cl.
   *C07K 14/475* (2006.01)

(52) U.S. Cl. .................................. 530/399; 530/350

(58) Field of Classification Search ................ 530/350, 530/412, 399; 536/23.4; 435/69.1, 69.4
   See application file for complete search history.

(56) References Cited

U.S. PATENT DOCUMENTS

| 5,434,064 | A | 7/1995 | Schlessinger |
| 5,872,234 | A | 2/1999 | Bandman |
| 6,303,765 | B1 | 10/2001 | Bandman et al. |

FOREIGN PATENT DOCUMENTS

WO    WO-00/55633    9/2000

OTHER PUBLICATIONS

Fuchs, E., Current Opinion in Cell Biology, 2:1028-10354 (1990).

Fuchs, E.J., J. Cell Biol., 111 (6/Pt. 2):2807-2814 (1990).
Backendorf, et al., Nature Genetics, 2:91 (1992).
Steinert, et al., Intl. J. Macromol., 13(3):130-139 (1991).
Volz, et al., Genomics, 18:92-99 (1993).
Johnson, et al., The 46th Annual Meeting of the American Society of Human Genetics, San Francisco, CA, Abstract No. 2316 (1996).
Smits, et al., The 25th European Symposium on Calcified Tissues, European Calcified Tissue Society, Harrogate, UK, Abstract No. P222 (1997).
Johnson, et al., Genbank Accession No. U65934 (Aug. 13, 1996).
Johnson, et al., Genbank Accession No. U65932 (Aug. 13, 1996).
Genbank Accession No. Q16610 (1996).
GenBank Accession No. R83319, "yp82e01.s1 Soares fetal liver spleen INFLS *Homo sapiens* cDNA clone Image:193944 3', mRNA sequence," Hillier, et al. (Aug. 4, 1995).
Bhalerao, et al., J. Biol. Chem., 270:16385-16394.
GenBank Accession No. R98765, "yq67d11.s1 Soares fetal liver spleen INFLS *Homo sapiens* cDNA clone Image:100853 3', mRNA sequence," Hillier, et al. (Sep. 13, 1995).
GenBank Accession No. N71368, "za31b08.s1 Soares fetal liver spleen INFLS *Homo sapiens* cDNA clone Image:294135 3', mRNA sequence," Hillier, et al. (Mar. 14, 1996).
GenBank Accession No. N71317, "za30b08.s1 Soares fetal liver spleen INFLS *Homo sapiens* cDNA clone Image:193944 3', mRNA sequence," Hillier, et al. (Mar. 14, 1996).
GenBank Accession No. H66729, "yr83e091.s1 Soares fetal liver spleen INFLS *Homo sapiens* cDNA clone Image:211912 3', mRNA sequence," Hiller, et al. (Oct. 18, 1995).

(Continued)

*Primary Examiner*—Brenda Brumback
*Assistant Examiner*—Daniel C. Gamett
(74) *Attorney, Agent, or Firm*—Human Genome Sciences, Inc.

(57) ABSTRACT

A human epidermal differentiation factor polypeptide and DNA (RNA) encoding such polypeptide and procedure for producing such polypeptide by recombinant techniques is disclosed. Also disclosed are methods for utilizing such polypeptide for treating and/or preventing skin diseases. Diagnostic assays for detecting mutations in a nucleic acid sequence encoding a polypeptide of the present invention and for detecting altered levels of the polypeptide of the present invention are also disclosed.

27 Claims, 2 Drawing Sheets

OTHER PUBLICATIONS

GenBank Accession No. R62808, "yi11c04.s1 Soares placenta Nb2HP Homo sapiens cDNA clone Image:138918 3', mRNA sequence," Hiller, et al. (May 26, 1995).

GenBank Accession No. H66472, "yu51h12.s1 Soares fetal liver spleen INFLS *Homo sapiens* cDNA clone Image: 229703 3', mRNA sequence," Hillier, et al. (Oct. 18, 1995).

Deckers, et al., "Recombinant human extracellular matrix protein 1 inhibits alkaline phosphatase activity and minerlization of mouse embryonic metatarsals in vitro," Bone, 28(1):14-20 (2001).

Locus Link Locus ID:1893, "ECM1:extracellular matrix protein 1," NCBI.

OMIM Accession No. 602201, "Extracellular matrix protein 1; ECM1," Johns Hopkins University (Jan. 12, 1998).

GenBank Accession No. NM_04425, "*Homo sapiens* extracellular matrix protein 1 (ECM1), transcript variant 1" (Feb. 7, 2001).

GenBank Accession No. NP_04416, "Extracellular matrix protein 1, isoform 1 precursor; secretory component p85" (Feb. 7, 2001).

GenBank Accession No. NM_022664, "*Homo sapiens* extracellular matrix protein 1 (ECM1) transcript variant 2" (Feb. 7, 2001).

GenBank Accession No. NP_073155, "Extracellular matrix protein 1, isoform 2 precursor; secretory component p85" (Feb. 7, 2001).

Smits, et al., "Differentiation-dependent alternative splicing and expression of the extracellular matrix protein 1 gene in human keratinocytes," J. Investigative Dermatology, 114(4):718-724 (2000).

Han, et al., "Extracellular matrix protein 1 (ECM1) has angiogenic properties and is expressed by breast tumor cells," FASEB Journal, 15:988-994 (2001).

Smits, et al., "The human extracellular matrix gene 1 (ECM1): genomic structure, cDNA cloning, expression pattern, and chromosomal localization," Genomics, 45:487-495 (1997).

Hamada, et al., "Lipoid proteinosis maps to 1q21 and is caused by mutations in the extracellular matrix protein 1 gene (ECM1)," Hum. Mol. Gen., 11(7):833-840 (2002).

```
              -50                    -30                   -10
     ATGGGGACCACAGCCAGAGCAGCCTTGGTCTTGACCTATTTGGCTGTTGCTTCTGCTGCC
      M  G  T  T  A  R  A  A  A  L  V  L  T  Y  L  A  V  A  S  A  A
              10                    30                   50
     TCTGAGGGAGGCTTCACGGCTACAGGACAGAGGCAGCTGAGGCCAGAGCACTTTCAAGAA
      S  E  G  G  F  T  A  T  G  Q  R  Q  L  R  P  E  H  F  Q  E
              70                    90                  110
     GTTGGCTACGCAGCTCCCCCCTCCCCACCCCTATCCCGAAGCCTCCCCATGGATCACCCT
      V  G  Y  A  A  P  P  S  P  P  L  S  R  S  L  P  M  D  H  P
              130                   150                 170
     GACTCCTCTCAGCATGGCCCTCCCTTTGAGGGACAGAGTCAAGTGCAGCCCCCTCCCTCT
      D  S  S  Q  H  G  P  P  F  E  G  Q  S  Q  V  Q  P  P  P  S
              190                   210                 230
     CAGGAGGCCACCCCTCTCCAACAGGAAAAGCTGCTACCTGCCCAACTCCCTGCTGAAAAG
      Q  E  A  T  P  L  Q  Q  E  K  L  L  P  A  Q  L  P  A  E  K
              250                   270                 290
     GAAGTGGGTCCCCCTCTCCCTCAGGAAGCTGTCCCCCTCCAAAAAGAGCTGCCCTCTCTC
      E  V  G  P  P  L  P  Q  E  A  V  P  L  Q  K  E  L  P  S  L
              310                   330                 350
     CAGCACCCCAATGAACAGAAGGAAGGAACGCCAGCTCCATTTGGGGACCAGAGCCATCCA
      Q  H  P  N  E  Q  K  E  G  T  P  A  P  F  G  D  Q  S  H  P
              370                   390                 410
     GAACCTGAGTCCTGGAATGCAGCCCAGCACTGCCAACAGGACCGGTCCCAAGGGGGCTGG
      E  P  E  S  W  N  A  A  Q  H  C  Q  Q  D  R  S  Q  G  G  W
              430                   450                 470
     GGCCACCGGCTGGATGGCTTCCCCCCTGGGCGGCCTTCTCCAGACAATCTGAACCAAATC
      G  H  R  L  D  G  F  P  P  G  R  P  S  P  D  N  L  N  Q  I
              490                   510                 530
     TGCCTTCCTAACCGTCAGCATGTGGTATATGGTCCCTGGAACCTACCACAGTCCAGCTAC
      C  L  P  N  R  Q  H  V  V  Y  G  P  W  N  L  P  Q  S  S  Y
              550                   570                 590
     TCCCACCTCACTCGCCAGGGTGAGACCCTCAATTTCCTGGAGATTGGATATTCCCGCTGC
      S  H  L  T  R  Q  G  E  T  L  N  F  L  E  I  G  Y  S  R  C
              610                   630                 650
     TGCCACTGCCGGCAGCCACACAAACCGCCTAGAGTGTGCCAAACTTGTGTGGGAGGATACC
      C  H  C  R  S  H  T  N  R  L  E  C  A  K  L  V  W  E  D  T
              670                   690                 710
     CTTGACAAATACTGTGACCGGGAGTATGCTGTGAAGACCCACCACCACTTGTGTTGCCGC
      L  D  K  Y  C  D  R  E  Y  A  V  K  T  H  H  H  L  C  C  R
              730                   750                 770
     CACCCTCCCAGCCCTACTCGGGATGAGTGTTTTGCCCGTCGGGCTCCTTACCCCAACTAT
      H  P  P  S  P  T  R  D  E  C  F  A  R  R  A  P  Y  P  N  Y
              790                   810                 830
     GACCGGGACATCTTGACCATTGACATCAGTCGAGTCACCCCCAACCTCATGGGCCACCTC
      D  R  D  I  L  T  I  D  I  S  R  V  T  P  N  L  M  G  H  L
              850                   870                 890
     TGTGGAAACCAAAGAGTTCTCACCAAGCATAAACATATTCCTGGGCTGATCCACAACATG
      C  G  N  Q  R  V  L  T  K  H  K  H  I  P  G  L  I  H  N  M
              910                   930                 950
     ACTGCCCGCTGCTGTGACCTGCCATTTCCAGAACAGGCCTGCTGTGCAGAGGAGGAGAAA
      T  A  R  C  C  D  L  P  F  P  E  Q  A  C  C  A  E  E  E  K
              970                   990                1010
     TTAACCTTCATCAATGATCTGTGTGGTCCCCGACGTAACATCTGGCGAGACCCTGCCCTC
      L  T  F  I  N  D  L  C  G  P  R  R  N  I  W  R  D  P  A  L
              1030                  1050                1070
     TGCTGTTACCTGAGTCCTGGGGATGAACAGGTCAACTGCTTCAACATCAATTATCTGAGG
      C  C  Y  L  S  P  G  D  E  Q  V  N  C  F  N  I  N  Y  L  R
              1090                  1110                1130
     AACGTGGCTCTAGTGTCTGGAGACACTGAGAACGCCAAGGGCCAGGGGCAGCAGGGCTCA
      N  V  A  L  V  S  G  D  T  E  N  A  K  G  Q  G  Q  Q  G  S
              1150                  1170                1190
     ACTGGAGGAACAAATATCAGCTCCACCTCTGAGCCCAAGGAAGAATGAGTCACCCCAGAG
      T  G  G  T  N  I  S  S  T  S  E  P  K  E  E  *
              1210                  1230                1250
     CCCTAGAGGGTCAGATGGGGGGAACCCCACCCTGCCCCACCCATCTGAACACTCATTACA
              1270                  1290
     CTAAACACCTCTTGGATTTGGTGTCAAAAAAAAAAAAAAAAAA
```

FIG. 1

```
  1 MGTTARAALVLTYLAVASAASEGGFTATGQRQLRPE....HFQEVGYAAP  46
    |||..||||:|.:||:|||||||:|.|.:||::  ||    |::|||||||
  1 MGTVSRAALILACLALASAASEGAFKASDQREMTPERLFQHLHEVGYAAP  50

47 PSPPLSRSLPMDHPDSSQHGPP.FEGQSQVQPPPSQEATPLQQEKLLPAQ  95
    || |  .|.|.:||. .| |:|| ||:|.:||||.|.|..|: :|.:.
 51 PSLPQTRRLRVDHSVTSLHDPPLFEEQREVQPPSSPEDIPVYEEDWPTFL 100

96 LPAEKEVGPPLPQEAVPLQKELPSLQHPNEQKEGTPAP............ 133
    |.  ...||::|||||:|||||  |.  |  ||||   .|::
101 NPNVDKAGPAVPQEAIPLQKEQPPPQVHIEQKEIDPPAQPQEEIVQKEVK 150

134 ...FGDQSHPEPESWNAAQHCQQDRSQGGWGHRLDGFPPGRPSPDNLNQI 180
       :::| .||| .||:|.||||:|  .|.||||||||||||||||.||
151 PHTLAGQLPPEPRTWNPARHCQQGR.RGVWGHRLDGFPPGRPSPDNLKQI 199

181 CLPNRQHVVYGPWNLPQSSYSHLTRQGETLNFLEIGYSRCCHCRSHTNRL 230
    |||:||||:|||||||||:|||.:||||||.||||||.||.||||||
200 CLPERQHVIYGPWNLPQTGYSHLSRQGETLNVLETGYSRCCPCRSDTNRL 249

231 ECAKLVWED......................................... 239
    :| ||||||
250 DCLKLVWEDAMTQFCEAEFSVKTRPHLCCRLRGEERFSCFQKEAPRPDYL 299

239 .................................................. 240

300 LRPCPVHQNGMSSGPQLPFPPGLPTPDNVKNICLLRRFRAVPRNLPATDA 349

240 ...........................TLDKYCDREYAVKTHH        255
                               |||  ||:||.|:|||.
350 IQRQLQALTRLETEFQRCCRQGHNHTCTWKAWEGTLDGYCERELAIKTHP 399

256 HLCCRHPPSPTRDECFARRAPYPNYDRDILTIDISRVTPNLMGHLCGNQR 305
    | ||:.|||.|||||||: |||||||||||:|:||||||||||:|||..|
400 HSCCHYPPSPARDECFAHLAPYPNYDRDILTLDLSRVTPNLMGQLCGSGR 449

306 VLTKHKHIPGLIHNMTARCCDLPFPEQACCAEEEKLTFINDLCGPRRNIW 355
    ||.|||:||||:|||.|||:||||||||||||||||.||::|||||||||  |
450 VLSKHKQIPGLIQNMTVRCCELPYPEQACCGEEEKLAFIENLCGPRRNSW 499

356 RDPALCCYLSPGDEQVNCFNINYLRNVALVSGDTENAKGQGEQGSTGGTN 405
    :||||||  |||:|.:|||||||.||||||||.|||:||.|  ||||.| ||:
500 KDPALCCDLSPEDKQINCFNTNYLRNVALVAGDTGNATGLGEQGPTRGTD 549

406 ISSTSEPKEE                                          415
    ......:.|||
550 ANPAPGSKEE                                          559
```

FIG. 2

SEQUENCE LISTING

<160> NUMBER OF SEQ ID NOS: 7

<210> SEQ ID NO 1
<211> LENGTH: 1354
<212> TYPE: DNA
<213> ORGANISM: Homo sapiens
<220> FEATURE:
<221> NAME/KEY: CDS
<222> LOCATION: (1)..(1248)
<223> OTHER INFORMATION:
<220> FEATURE:
<221> NAME/KEY: sig_peptide
<222> LOCATION: (1)..(57)
<223> OTHER INFORMATION:
<220> FEATURE:
<221> NAME/KEY: mat_peptide
<222> LOCATION: (58)..(1245)
<223> OTHER INFORMATION:

<400> SEQUENCE: 1

```
atg ggg acc aca gcc aga gca gcc ttg gtc ttg acc tat ttg gct gtt      48
Met Gly Thr Thr Ala Arg Ala Ala Leu Val Leu Thr Tyr Leu Ala Val
            -15                 -10                  -5 gct tct gct gcc tct gag gga ggc ttc acg gct aca gga cag agg cag      96
Ala Ser Ala Ala Ser Glu Gly Gly Phe Thr Ala Thr Gly Gln Arg Gln
         -1  1                5                  10 ctg agg cca gag cac ttt caa gaa gtt ggc tac gca gct ccc ccc tcc     144
Leu Arg Pro Glu His Phe Gln Glu Val Gly Tyr Ala Ala Pro Pro Ser
        15                  20                  25 cca ccc cta tcc cga agc ctc ccc atg gat cac cct gac tcc tct cag     192
Pro Pro Leu Ser Arg Ser Leu Pro Met Asp His Pro Asp Ser Ser Gln
30                  35                  40                  45
```

```
cat ggc cct ccc ttt gag gga cag agt caa gtg cag ccc cct ccc tct      240
His Gly Pro Pro Phe Glu Gly Gln Ser Gln Val Gln Pro Pro Pro Ser
             50                  55                  60 cag gag gcc acc cct ctc caa cag gaa aag ctg cta cct gcc caa ctc      288
Gln Glu Ala Thr Pro Leu Gln Gln Glu Lys Leu Leu Pro Ala Gln Leu
             65                  70                  75 cct gct gaa aag gaa gtg ggt ccc cct ctc cct cag gaa gct gtc ccc      336
Pro Ala Glu Lys Glu Val Gly Pro Pro Leu Pro Gln Glu Ala Val Pro
         80                  85                  90 ctc caa aaa gag ctg ccc tct ctc cag cac ccc aat gaa cag aag gaa      384
Leu Gln Lys Glu Leu Pro Ser Leu Gln His Pro Asn Glu Gln Lys Glu
         95                 100                 105 gga acg cca gct cca ttt ggg gac cag agc cat cca gaa cct gag tcc      432
Gly Thr Pro Ala Pro Phe Gly Asp Gln Ser His Pro Glu Pro Glu Ser
110                 115                 120                 125 tgg aat gca gcc cag cac tgc caa cag gac cgg tcc caa ggg ggc tgg      480
Trp Asn Ala Ala Gln His Cys Gln Gln Asp Arg Ser Gln Gly Gly Trp
                130                 135                 140 ggc cac cgg ctg gat ggc ttc ccc cct ggg cgg cct tct cca gac aat      528
Gly His Arg Leu Asp Gly Phe Pro Pro Gly Arg Pro Ser Pro Asp Asn
                145                 150                 155 ctg aac caa atc tgc ctt cct aac cgt cag cat gtg gta tat ggt ccc      576
Leu Asn Gln Ile Cys Leu Pro Asn Arg Gln His Val Val Tyr Gly Pro
                160                 165                 170 tgg aac cta cca cag tcc agc tac tcc cac ctc act cgc cag ggt gag      624
Trp Asn Leu Pro Gln Ser Ser Tyr Ser His Leu Thr Arg Gln Gly Glu
            175                 180                 185 acc ctc aat ttc ctg gag att gga tat tcc cgc tgc tgc cac tgc cgc      672
Thr Leu Asn Phe Leu Glu Ile Gly Tyr Ser Arg Cys Cys His Cys Arg
190                 195                 200                 205 agc cac aca aac cgc cta gag tgt gcc aaa ctt gtg tgg gag gat acc      720
Ser His Thr Asn Arg Leu Glu Cys Ala Lys Leu Val Trp Glu Asp Thr
                210                 215                 220 ctt gac aaa tac tgt gac cgg gag tat gct gtg aag acc cac cac cac      768
Leu Asp Lys Tyr Cys Asp Arg Glu Tyr Ala Val Lys Thr His His His
                225                 230                 235 ttg tgt tgc cgc cac cct ccc agc cct act cgg gat gag tgt ttt gcc      816
Leu Cys Cys Arg His Pro Pro Ser Pro Thr Arg Asp Glu Cys Phe Ala
            240                 245                 250 cgt cgg gct cct tac ccc aac tat gac cgg gac atc ttg acc att gac      864
Arg Arg Ala Pro Tyr Pro Asn Tyr Asp Arg Asp Ile Leu Thr Ile Asp
            255                 260                 265 atc agt cga gtc acc ccc aac ctc atg ggc cac ctc tgt gga aac caa      912
Ile Ser Arg Val Thr Pro Asn Leu Met Gly His Leu Cys Gly Asn Gln
270                 275                 280                 285 aga gtt ctc acc aag cat aaa cat att cct ggg ctg atc cac aac atg      960
Arg Val Leu Thr Lys His Lys His Ile Pro Gly Leu Ile His Asn Met
                290                 295                 300 act gcc cgc tgc tgt gac ctg cca ttt cca gaa cag gcc tgc tgt gca     1008
Thr Ala Arg Cys Cys Asp Leu Pro Phe Pro Glu Gln Ala Cys Cys Ala
                305                 310                 315 gag gag gag aaa tta acc ttc atc aat gat ctg tgt ggt ccc cga cgt     1056
Glu Glu Glu Lys Leu Thr Phe Ile Asn Asp Leu Cys Gly Pro Arg Arg
            320                 325                 330 aac atc tgg cga gac cct gcc ctc tgc tgt tac ctg agt cct ggg gat     1104
Asn Ile Trp Arg Asp Pro Ala Leu Cys Cys Tyr Leu Ser Pro Gly Asp
            335                 340                 345 gaa cag gtc aac tgc ttc aac atc aat tat ctg agg aac gtg gct cta     1152
Glu Gln Val Asn Cys Phe Asn Ile Asn Tyr Leu Arg Asn Val Ala Leu
```

-continued

```
                350                 355                 360                 365
gtg tct gga gac act gag aac gcc aag ggc cag ggg gag cag ggc tca       1200
Val Ser Gly Asp Thr Glu Asn Ala Lys Gly Gln Gly Glu Gln Gly Ser
                370                 375                 380 act gga gga aca aat atc agc tcc acc tct gag ccc aag gaa gaa           1245
Thr Gly Gly Thr Asn Ile Ser Ser Thr Ser Glu Pro Lys Glu Glu
            385                 390                 395 tgagtcaccc cagagcccta gagggtcaga tgggggaac cccaccctgc cccacccatc      1305
tgaacactca ttacactaaa cacctcttgg atttggtgtc aaaaaaaaa                 1354
```

<210> SEQ ID NO 2
<211> LENGTH: 415
<212> TYPE: PRT
<213> ORGANISM: Homo sapiens

<400> SEQUENCE: 2

```
Met Gly Thr Thr Ala Arg Ala Ala Leu Val Leu Thr Tyr Leu Ala Val
                -15                 -10                 -5

Ala Ser Ala Ala Ser Glu Gly Gly Phe Thr Ala Thr Gly Gln Arg Gln
     -1   1                   5                      10

Leu Arg Pro Glu His Phe Gln Glu Val Gly Tyr Ala Ala Pro Pro Ser
         15                  20                  25

Pro Pro Leu Ser Arg Ser Leu Pro Met Asp His Pro Asp Ser Ser Gln
30                  35                  40                  45

His Gly Pro Pro Phe Glu Gly Gln Ser Gln Val Gln Pro Pro Pro Ser
                50                  55                  60

Gln Glu Ala Thr Pro Leu Gln Gln Glu Lys Leu Leu Pro Ala Gln Leu
                65                  70                  75

Pro Ala Glu Lys Glu Val Gly Pro Pro Leu Pro Gln Glu Ala Val Pro
            80                  85                  90

Leu Gln Lys Glu Leu Pro Ser Leu Gln His Pro Asn Glu Gln Lys Glu
        95                  100                 105

Gly Thr Pro Ala Pro Phe Gly Asp Gln Ser His Pro Glu Pro Glu Ser
110                 115                 120                 125

Trp Asn Ala Ala Gln His Cys Gln Gln Asp Arg Ser Gln Gly Gly Trp
                130                 135                 140

Gly His Arg Leu Asp Gly Phe Pro Pro Gly Arg Pro Ser Pro Asp Asn
            145                 150                 155

Leu Asn Gln Ile Cys Leu Pro Asn Arg Gln His Val Val Tyr Gly Pro
        160                 165                 170

Trp Asn Leu Pro Gln Ser Ser Tyr Ser His Leu Thr Arg Gln Gly Glu
    175                 180                 185

Thr Leu Asn Phe Leu Glu Ile Gly Tyr Ser Arg Cys Cys His Cys Arg
190                 195                 200                 205

Ser His Thr Asn Arg Leu Glu Cys Ala Lys Leu Val Trp Glu Asp Thr
                210                 215                 220

Leu Asp Lys Tyr Cys Asp Arg Glu Tyr Ala Val Lys Thr His His His
            225                 230                 235

Leu Cys Cys Arg His Pro Pro Ser Pro Thr Arg Asp Glu Cys Phe Ala
        240                 245                 250

Arg Arg Ala Pro Tyr Pro Asn Tyr Asp Arg Asp Ile Leu Thr Ile Asp
    255                 260                 265

Ile Ser Arg Val Thr Pro Asn Leu Met Gly His Leu Cys Gly Asn Gln
270                 275                 280                 285
```

-continued

```
Arg Val Leu Thr Lys His Lys His Ile Pro Gly Leu Ile His Asn Met
            290                 295                 300
Thr Ala Arg Cys Cys Asp Leu Pro Phe Pro Glu Gln Ala Cys Cys Ala
            305                 310                 315
Glu Glu Glu Lys Leu Thr Phe Ile Asn Asp Leu Cys Gly Pro Arg Arg
            320                 325                 330
Asn Ile Trp Arg Asp Pro Ala Leu Cys Cys Tyr Leu Ser Pro Gly Asp
            335                 340                 345
Glu Gln Val Asn Cys Phe Asn Ile Asn Tyr Leu Arg Asn Val Ala Leu
350                 355                 360                 365
Val Ser Gly Asp Thr Glu Asn Ala Lys Gly Gln Gly Glu Gln Gly Ser
            370                 375                 380
Thr Gly Gly Thr Asn Ile Ser Ser Thr Ser Glu Pro Lys Glu Glu
            385                 390                 395
```

<210> SEQ ID NO 3
<211> LENGTH: 32
<212> TYPE: DNA
<213> ORGANISM: Artificial sequence
<220> FEATURE:
<223> OTHER INFORMATION: Contains a BamHI restriction site and a signal
      for initiation of translation in eukaryotic cells

<400> SEQUENCE: 3
cgggatccgc catcatgggg acccacagcc ag                                32

<210> SEQ ID NO 4
<211> LENGTH: 26
<212> TYPE: DNA
<213> ORGANISM: Artificial sequence
<220> FEATURE:
<223> OTHER INFORMATION: Contains an XbaI restriction site

<400> SEQUENCE: 4
gctctagatc caagaggtgt ttagtg                                       26

<210> SEQ ID NO 5
<211> LENGTH: 27
<212> TYPE: DNA
<213> ORGANISM: Artificial sequence
<220> FEATURE:
<223> OTHER INFORMATION: Contains a BamHI restriction site

<400> SEQUENCE: 5
cgcggatcca ccatggggac cacagcc                                      27

<210> SEQ ID NO 6
<211> LENGTH: 54
<212> TYPE: DNA
<213> ORGANISM: Artificial sequence
<220> FEATURE:
<223> OTHER INFORMATION: Contains an XbaI restriction site, translation
      stop codon, and an HA tag

<400> SEQUENCE: 6
cgctctagat caagcgtagt ctgggacgtc gtatgggtat tcttccttgg gctc         54

<210> SEQ ID NO 7
<211> LENGTH: 434
<212> TYPE: PRT
<213> ORGANISM: Mus musculus

<400> SEQUENCE: 7

-continued

```
Met Gly Thr Val Ser Arg Ala Ala Leu Ile Leu Ala Cys Leu Ala Leu
 1               5                  10                  15

Ala Ser Ala Ala Ser Glu Gly Ala Phe Lys Ala Ser Asp Gln Arg Glu
            20                  25                  30

Met Thr Pro Glu Arg Leu Phe Gln His Leu His Glu Val Gly Tyr Ala
                35                  40                  45

Ala Pro Pro Ser Leu Pro Gln Thr Arg Arg Leu Arg Val Asp His Ser
        50                  55                  60

Val Thr Ser Leu His Asp Pro Pro Leu Phe Glu Glu Gln Arg Glu Val
 65                  70                  75                  80

Gln Pro Pro Ser Ser Pro Glu Asp Ile Pro Val Tyr Glu Glu Asp Trp
                85                  90                  95

Pro Thr Phe Leu Asn Pro Asn Val Asp Lys Ala Gly Pro Ala Val Pro
                100                 105                 110

Gln Glu Ala Ile Pro Leu Gln Lys Glu Gln Pro Pro Gln Val His
            115                 120                 125

Ile Glu Gln Lys Glu Ile Asp Pro Pro Ala Gln Pro Gln Glu Glu Ile
130                 135                 140

Val Gln Lys Glu Val Lys Pro His Thr Leu Ala Gly Gln Leu Pro Pro
145                 150                 155                 160

Glu Pro Arg Thr Trp Asn Pro Ala Arg His Cys Gln Gln Gly Arg Arg
                165                 170                 175

Gly Val Trp Gly His Arg Leu Asp Gly Phe Pro Pro Gly Arg Pro Ser
                180                 185                 190

Pro Asp Asn Leu Lys Gln Ile Cys Leu Pro Glu Arg Gln His Val Ile
        195                 200                 205

Tyr Gly Pro Trp Asn Leu Pro Gln Thr Gly Tyr Ser His Leu Ser Arg
        210                 215                 220

Gln Gly Glu Thr Leu Asn Val Leu Glu Thr Gly Tyr Ser Arg Cys Cys
225                 230                 235                 240

Pro Cys Arg Ser Asp Thr Asn Arg Leu Asp Cys Leu Lys Leu Val Trp
                245                 250                 255

Glu Gly Thr Leu Asp Gly Tyr Cys Glu Arg Glu Leu Ala Ile Lys Thr
                260                 265                 270

His Pro His Ser Cys Cys His Tyr Pro Pro Ser Pro Ala Arg Asp Glu
                275                 280                 285

Cys Phe Ala His Leu Ala Pro Tyr Pro Asn Tyr Asp Arg Asp Ile Leu
        290                 295                 300

Thr Leu Asp Leu Ser Arg Val Thr Pro Asn Leu Met Gly Gln Leu Cys
305                 310                 315                 320

Gly Ser Gly Arg Val Leu Ser Lys His Lys Gln Ile Pro Gly Leu Ile
                325                 330                 335

Gln Asn Met Thr Val Arg Cys Cys Glu Leu Pro Tyr Pro Glu Gln Ala
                340                 345                 350

Cys Cys Gly Glu Glu Lys Leu Ala Phe Ile Glu Asn Leu Cys Gly
            355                 360                 365

Pro Arg Arg Asn Ser Trp Lys Asp Pro Ala Leu Cys Cys Asp Leu Ser
        370                 375                 380

Pro Glu Asp Lys Gln Ile Asn Cys Phe Asn Thr Asn Tyr Leu Arg Asn
385                 390                 395                 400
```

-continued

```
Val Ala Leu Val Ala Gly Asp Thr Gly Asn Ala Thr Gly Leu Gly Glu
            405                 410                 415

Gln Gly Pro Thr Arg Gly Thr Asp Ala Asn Pro Ala Pro Gly Ser Lys
            420                 425                 430

Glu Glu
```

EPIDERMAL DIFFERENTIATION FACTOR

CROSS REFERENCE TO RELATED APPLICATIONS

This application is a continuation of application Ser. No. 10/192,634, filed Jul. 11, 2002, now abandoned, which is a continuation of application Ser. No. 09/317,850 filed on May 25, 1999, now abandoned, which is a divisional of application Ser. No. 08/815,718 filed on Mar. 12, 1997 (now issued U.S. Pat. No. 5,981,220), which is a non-provisional application, and claims benefit of priority under 35 U.S.C. § 119(e), of provisional Application No. 60/014,220 filed on Mar. 27, 1996. Each of the above referenced applications is herein incorporated by reference in its entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as an epidermal differentiation factor, sometimes hereinafter referred to as "EDF". The invention also relates to inhibiting the action of such polypeptides.

BACKGROUND OF THE INVENTION

Cellular growth and differentiation appear to be initiated, promoted, maintained and regulated by a multiplicity of stimulatory, inhibitory and synergistic factors and hormones. The alteration and/or breakdown of the cellular homeostasis mechanism seems to be a fundamental cause of growth related diseases, including neoplasia. Growth modular factors are implicated in a wide variety of pathological and physiological processes including signal transduction, cell communication, growth and development, embryo genesis, immune response, hematopoiesis cell survival and differentiation, inflammation, tissue repair and remodeling, atherosclerosis and cancer.

Epidermal growth factor (EGF), transforming growth factor alpha (TGFα), betacellulin, amphiregulin, and vaccinia growth factor among other factors are growth and differentiation modulatory proteins induced by a variety of cell types either under normal physiological conditions or in response to exogenous stimuli.

These peptide growth factors influence wound cells through autocrine and paracrine mechanisms. They also play important roles in normal wound healing in tissues such as skin, cornea and gastrointestinal tract and they all share substantial amino acid sequence homology including the conserved placement of three intra-chain disulfide bonds. In addition, all the factors of this family bind to a 170,000 molecular weight transmembrane glycoprotein receptor and activate the tyrosine kinase activity in the receptors cytoplasmic domain (Buhrow, S. A. et al., *J. Bio. Chem.*, 8:7824–7826 (1983).

The receptors are expressed by many types of cells including skin keratinocytes, fibroblasts, vascular endothelial cells and epithelial cells of the gastrointestinal tract. These peptide growth factors are synthesized by several cells involved in wound healing including platelets, keratinocytes, and activated macrophages. These growth factors have also been implicated in both the stimulation of growth and differentiation of certain cells.

A protein which migrates as a train of spots with an average mass of 85 kda has been disclosed (Bhalerao, et al., *J. Bio. Chem.*, 279(27):16385–16294 (1995)). This protein has been designated as "p85". The full length cDNA contains an open reading frame of 1,677 base pairs encoding a protein of 559 amino acids. Computer analysis of the deduced primary amino acid sequence reveals a hydrophobic signal peptide characteristic of a secreted protein. Motif analysis did not identify features typical for known protein families. The message of 1.9 kb is expressed in various tissues such as liver, heart, lungs, etc., whereas a splice variant was present in embryonic cartilage and skin. The corresponding gene for p85 (called ECM1 for extracellular matrix protein 1), maps on chromosome 3 of the mouse in a region containing several loci involved in skin development disorders. p85 was originally identified as a novel secreted protein of the mouse stromal osteogenic cell line, MN7.

The gene maps to chromosome 3, just distal to GBA in a region containing at least 3 known mutations affecting skin: FT (flaky tail), SOC (soft coat), and MA (matted). This suggests that the p85 gene may represent a candidate for any of these mutations. In particular, mice with SOC have abnormalities in the epidermis, hair bowl, whiskers and display a clumping of the hairs of the coat (Green, M. C. (1989)) in genetic variance and strains of the laboratory mouse (Lyon, M. F. and Searle, A. G., EDS) pp. 12–403, Oxford University Press, Oxford, all of which is consistent with the known expression pattern of ECM1. Correlation of SOC and ECM1 would provide important information in the elucidation of the in vivo function of p85.

The localization of ECM1 is also interesting from another standpoint. The ECM1 region shares linkage homology to human chromosome 1q21 (O'Brien, S. J. and Graves, M. J. A. (1991), Cytogenet. Cell Genet. 58:1124–1151), a region that contained a cluster of 3 families of genes involved in epidermal differentiation (Volz, A. et al., *Genomics*, 18:92–99 (1993)). One family includes the proteins loricrin, involucrin and a small proline-rich protein. These proteins are closely associated in the formation of the cornified cell envelope in the uppermost layers of the epidermis (Yoneda, K. et al., *J. Biol. Chem.*, 267:18060–18066 (1992)). Each of these genes contains a region of short tandem peptide repeats that have been partially conserved during evolution (Steinert, P. M. et al., *J. Biol. Macromol.*, 13:130–139 (1991)). A recent report demonstrated that the mouse homologue of loricrin maps to mouse chromosome 3 in apparent close proximity to ECM1 (Rothnagel, J. A. et al., *Genomics*, 23:450–456 (1994)).

The second group includes several members of the S100 family of small calcium-binding proteins. These proteins contain 2 calcium binding domains with the EF-hand motif, are highly homologous at the amino acid sequence level, and have a similar gene organization.

The third family localized to human 1q21 includes profilagrin and trichohyalin (Lee, S. C. et al., *J. Invest. Dermatol.*, 100:65–69 (1993)). These genes appear to be fused genes containing at the 5' end two EF-hand calcium finding motifs like those of the S100 family, and tandem repeats that are characteristic of the cornified cell envelope family (Markova, N. G., Mol. Cell. Biol., 13:613–625 (1993)). The mouse profilagrin locus has recently been mapped to chromosome 3 (Rothnagel, J. A. et al., *Genomics*, 23:450–456 (1994)).

The close physical linkage of these genes and the striking similarity in their organizations has been suggested to be the result of a common evolution (Bakendorf, C. and Hohl, D., Nature Genet., 2:91 (1992)). It has been suggested that some of these genes may share common regulatory regions and may function in concert during the final steps of epidermal differentiation (Rosenthal, D. S. et al., *J. Invest. Dermatol.*, 98:343–350 (1992)).

BRIEF SUMMARY OF THE INVENTION

The polypeptide of the present invention has been putatively identified as EDF as a result of linkage homology to human chromosome 1q21, the region that contains a cluster of three families of genes involving epidermal differentiation.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, cDNAs, genomic DNAs as well as analogs and biologically active and diagnostically or therapeutically useful fragments thereof.

In accordance with another aspect of the present invention there is provided an isolated nucleic acid molecule encoding a mature polypeptide expressed by the human cDNA contained in ATCC™ Deposit No. 97407.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to stimulate hematopoietic cell growth, to treat skin diseases, promote bone formation for healing of bone fractures and treatment of osteoporosis and osteogenesis imperfecta.

In accordance with yet a further aspect of the present invention, there are provided antibodies against such polypeptides.

In accordance with another aspect of the present invention, there are provided EDF agonists which mimic EDF and bind to EDF receptors.

In accordance with yet another aspect of the present invention, there are provided antagonists to such polypeptides, which may be used to inhibit the action of such polypeptides, for example, in the treatment of osteodystrophy, osteohypertrophy, osteoma, osteopetrosis, osteoporosis and osteoblastoma.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 is an illustration of the cDNA and corresponding deduced amino acid sequence of the polypeptide of the present invention. Sequencing was performed using a 373 automated DNA sequencer (Applied Biosystems, Inc.).

FIG. 2 is an amino acid sequence comparison between the polypeptide of the present invention (top line) and murine p85 protein (bottom line) (SEQ ID NO:7).

DETAILED DESCRIPTION

In accordance with an aspect of the present invention, there is provided an isolated nucleic acid (polynucleotide) which encodes for the mature polypeptide having the deduced amino acid sequence of FIG. 1 (SEQ ID NO:2).

The polynucleotide of this invention was discovered in a cDNA library derived from human tonsils. It is structurally related to the murine p85 protein. It contains an open reading frame encoding a protein of 415 amino acid residues of which approximately the first 19 amino acids residues are the putative leader sequence such that the mature protein comprises 396 amino acids. The protein exhibits the highest degree of homology at the amino acid level to murine p85 with 66.667% identity and 78.986% similarity. EDF also shows the highest degree of homology at the nucleotide sequence level to murine p85 with 80% identity and 80% similarity over a 547 base pair stretch.

The clone was identified by its homology with the mouse Ecm1 splicing variant for, since splicing occurs at the same position both in mouse and human. Mouse splicing variant is specifically expressed in tail, front paw and skin of embryonic mice, and mapped to the region on mouse chromosome 3 know to contain at least three known mutations affecting skin: ft (flaky tail), soc (soft coat), and ma (matted), these loci are associated with developmental disorders of the skin.

In accordance with another aspect of the present invention there are provided isolated polynucleotides encoding a mature polypeptide expressed by the human cDNA contained in ATCC™ Deposit No. 97407, deposited with the American Type Culture Collection, 10801 University Boulevard, Manassas, Va. 20110, USA, on Jan. 2, 1996. The deposited material is a pBLUESCRIPT™ SK (−) vector (STRATAGENE™, La Jolla, Calif.) that contains the full-length EDF cDNA.

The deposit has been made under the terms of the Budapest Treaty on the International Recognition of the Deposit of Micro-organisms for purposes of Patent Procedure. The strain will be irrevocably and without restriction or condition released to the public upon the issuance of a patent. The deposit is provided merely as convenience to those of skill in the art and are not an admission that a deposit is required under 35 U.S.C. § 112. The sequence of the polynucleotide contained in the deposited material, as well as the amino acid sequence of the polypeptide encoded thereby, are controlling in the event of any conflict with any description of sequences herein. A license may be required to make, use or sell the deposited material, and no such license is hereby granted.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or may be a different coding sequence which coding sequence, as a result of the redundancy or degeneracy of the genetic code, encodes the same mature polypeptide as the DNA of FIG. 1 (SEQ ID NO:1).

The polynucleotide which encodes for the mature polypeptide of FIG. 1 (SEQ ID NO:2) may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) as well as variants of such polynucleotides which variants encode for a fragment, derivative or analog of the polypeptide of FIG. 1 (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell,* 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

Further preferred embodiments of the invention are polynucleotides that are at least 70% identical to a polynucleotide encoding the EDF polypeptide having the amino acid sequence set out in FIG. 1 (SEQ ID NO:2), and polynucleotides which are complementary to such polynucleotides. Alternatively, most highly preferred are polynucleotides that comprise a region that is at least 80% identical to a polynucleotide encoding the EDF polypeptide and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a diagnostic probe or as a PCR primer.

Thus, the present invention is directed to polynucleotides having at least a 70% identity, preferably an at least an 85% identity, more preferably at least 90% identity and most preferably at least a 95% identity to a polynucleotide which encodes the polypeptide of SEQ ID NO:2 and polynucleotides complementary thereto as well as portions thereof, which portions have at least 15 consecutive bases, preferably 30 consecutive bases, and most preferably at least 50 consecutive bases and to polypeptides encoded by such polynucleotides.

The present invention further relates to a polypeptide which has the deduced amino acid sequence of FIG. 1 (SEQ ID NO:2), as well as fragments, analogs and derivatives of such polypeptide.

The terms "fragment," "derivative" and "analog" when referring to the polypeptide of FIG. 1 (SEQ ID NO:2), means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 85% similarity (preferably at least 85% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBLUESCRIPT™ SK, pBSKS, pNH8A, pNH16a, pNH18A, pNH46A (STRATAGENE™); pTRC99a, pKK223-3, pKK233-3, pDR540, pRIT5 (PHARMACIA™); Eukaryotic: pWLNEO, pSV2CAT, pOG44, pXT1, pSG (STRATAGENE™) pSVK3, pBPV, pMSG, pSVL (PHARMACIA™). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and tip. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC™ 37017). Such commercial vectors include, for example, pKK223-3 (PHARMACIA™ Fine Chemicals, Uppsala, Sweden) and GEM1 (PROMEGA BIOTEC™, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

EDF may be employed to treat and/or prevent skin disease. Mutations in the EDF gene may lead to skin disorders such as pruritus, dermatitis, bacterial skin infections, superficial fungal infections, parasitic skin infections, viral skin infections, disorders of hair follicles and sebaceous glands, scaling papular diseases, inflammatory skin reactions, bullous diseases, disorders of cornification, pigmentary disorders, disorders of sweating and skin tumors.

EDF may also be employed to promote bone formation for healing of bone fractures and treatment of osteoporosis and osteogenesis imperfecta.

The polynucleotides and polypeptides of the present invention may be employed as research reagents and materials for discovery of treatments and diagnostics to human disease.

This invention provides a method for identification of the receptor for EDF. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to EDF, and a cDNA library created from this RNA is divided into pools and used to transfect COS cells or other cells that are not responsive to EDF. Transfected cells which are grown on glass slides are exposed to labeled EDF. EDF can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which enhance or block interaction of EDF with its receptor. As an example, a mammalian cell or membrane preparation expressing the EDF receptor would be incubated with labeled EDF in the presence of the compound. The ability of the compound to enhance or block this interaction could then be measured. Alternatively, the response of a known second messenger system following interaction of EDF with its receptor would be measured and compared in the presence or absence of the compound. Such second messenger systems include but are not limited to, cAMP guanylate cyclase, ion channels or phosphoinositide hydrolysis.

An example of a specific antagonist assay is a competitive inhibition assay, wherein a potential agonist and labelled EDF are combined in the presence of membrane bound EDF receptors or recombinant EDF receptors under appropriate conditions for binding. The number of EDF molecules bound to the receptor is an indication of the effectiveness of the potential antagonist.

Potential antagonists include an antibody, or in some cases, an oligopeptide, which binds to the polypeptide. Alternatively, a potential antagonist may be a closely related protein which binds to the receptor sites, however, they are inactive forms of the polypeptide and thereby prevent the action of EDF since receptor sites are occupied.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al., Science, 241:456 (1988); and Dervan et al., Science, 251: 1360 (1991)), thereby preventing transcription and the production of EDF. The antisense RNA oligonucleotide hybridizes to the mRNA in vivo and blocks translation of the mRNA molecule into EDF polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of EDF.

Potential antagonists include a small molecule which binds to and occupies the catalytic site of the polypeptide thereby making the catalytic site inaccessible to substrate such that normal biological activity is prevented. Examples of small molecules include but are not limited to small peptides or peptide-like molecules.

The antagonists may be employed to treat osteodystrophy, osteohypertrophy, osteoma, osteopetrosis, osteoporosis and osteoblastoma. The antagonists may be employed in a composition with a pharmaceutically acceptable carrier, e.g., as hereinafter described.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The EDF polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the ⊕-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14x, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of EDF.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., *Nature*, 324:163–166 (1986)) prior to analysis. RNA or cDNA may also be used for the same purpose. As an example, PCR primers complementary to the nucleic acid encoding EDF can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of EDF. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the EDF antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled EDF and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, *Immunology Today* 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acid. Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLES

Example 1

Cloning and Expression of EDF Using the Baculovirus Expression System

The DNA sequence encoding the full length EDF protein, ATCC™ # 97407, was amplified using PCR oligonucleotide primers corresponding to the 5' and 3' sequences of the gene: The 5' primer has the sequence 5'-CG<u>GGATCC</u>GCCATC <u>ATG</u>GGGACCCACAGCCAG-3' (SEQ ID NO:3) and contains a BamHI restriction enzyme site (in bold) followed by 6 nucleotides resembling an efficient signal for the initiation of translation in eukaryotic cells (Kozak, M., J. Mol. Biol., 196:947–950 (1987). The primer also contains 15 nucleotides of EDF coding sequence (the initiation codon for translation "ATG" is underlined).

The 3' primer has the sequence 5'-GCTCTAGATCCAA-GAGGTGTTTAGTG-3' (SEQ ID NO:4) and contains the cleavage site for the restriction endonuclease XbaI and 18 nucleotides complementary to the 3' non-translated sequence of the EDF gene. The amplified sequences were isolated from a 1% agarose gel using a commercially available kit (GENECLEAN™, BIO 101 Inc., La Jolla, Calif.). The fragment was then digested with the endonucleases BamHI and XbaI and then purified again on a 1% agarose gel. This fragment is designated F2.

The vector pRG1 (modification of pVL941 vector, discussed below) is used for the expression of the EDF protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI and XbaI. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and XbaI and then dephosphorylated using calf intestinal phosphatase by procedures known in the art. The DNA was then isolated from a 1% agarose gel using the commercially available kit (GENECLEAN™ BIO 101 Inc., La Jolla, Calif.). This vector DNA is designated V2.

Fragment F2 and the dephosphorylated plasmid V2 were ligated with T4 DNA ligase. *E. coli* HB101 cells were then transformed and bacteria identified that contained the plasmid (pBacEDF) with the EDF gene using the enzymes BamHI and XbaI. The sequence of the cloned fragment was confirmed by DNA sequencing.

5 µg of the plasmid pBacEDF was co-transfected with 1.0 µg of a commercially available linearized baculovirus ("BACULOGOLD™ baculovirus DNA", Pharmingen, San Diego, Calif.) using the lipofection method (Felgner et al., *Proc. Natl. Acad. Sci. USA*, 84:7413–7417 (1987)).

1 µg of BACULOGOLD™ virus DNA and 5 µg of the plasmid pBacEDF were mixed in a sterile well of a microtiter plate containing 50 µl of serum free Grace's medium (Life Technologies Inc., Gaithersburg, Md.). Afterwards 10 µl LIPOFECTIN™ (liposomes) plus 90 µl Grace's medium were added, mixed and incubated for 15 minutes at room temperature. Then the transfection mixture was added dropwise to the Sf9 insect cells (ATCC™ CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-EDF at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

Example 2

Expression of Recombinant EDF in COS Cells

The expression of plasmid, EDF HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, an SV40 intron and polyadenylation site. A DNA fragment encoding the entire EDF precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows: The DNA sequence encoding EDF, ATCC™ # 97407, was constructed by PCR using two primers: the 5' primer 5'-CGC GGATCCACCATGGGGACCACAGCC-3' (SEQ ID NO:5) contains a Bam HI site (underlined) followed by 15 nucleotides of EDF coding sequence starting from the initiation codon; the 3' sequence 5'-CGC TCTAGATCAAGCGTAGTCTGGGACGTCGTATGGGT-ATTCTTCCTTGGGCTC-3' (SEQ ID NO:6) contains complementary sequences to an Xba I site (underlined), translation stop codon, HA tag and the last 15 nucleotides of the EDF coding sequence (not including the stop codon). Therefore, the PCR product contains a Bam HI site, EDF coding sequence followed by HA tag fused in frame, a translation termination stop codon next to the HA tag, and an Xba I site. The PCR amplified DNA fragment and the vector, pcDNAI/Amp, were digested with Bam HI and Xba I restriction enzyme and ligated. The ligation mixture was transformed into *E. coli* strain SURE (available from STRATAGENE™ Cloning Systems, La Jolla) the transformed culture was plated on ampicillin media plates and resistant colonies were selected. Plasmid DNA was isolated from transformants and examined by restriction analysis for the presence of the correct fragment. For expression of the recombinant EDF, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the EDF HA protein was detected by radiolabeling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

Example 3

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

The invention claimed is:

1. An isolated polypeptide, selected from the group consisting of:
   (a) a polypeptide comprising amino acids −19 to 396 of SEQ ID NO:2;
   (b) a polypeptide comprising amino acids 1 to 396 of sequence of SEQ ID NO:2;
   (c) a polypeptide comprising the full-length Epidermal Differentiation Factor (EDF) polypeptide encoded by the human cDNA in ATCC™ Deposit No. 97407;
   (d) a polypeptide comprising the mature form of the EDF polypeptide encoded by the human cDNA in ATCC™ Deposit No. 97407,
   wherein said polypeptide is glycosylated.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. An isolated polypeptide comprising polypeptide (a), (b), (c), or (d) of claim 1, fused to a heterologous polypeptide.

7. An isolated polypeptide produced by a method comprising:
   (a) expressing the polypeptide of claim 1 by a cell; and
   (b) recovering said polypeptide.

8. An isolated polypeptide selected from the group consisting of:
   (a) a polypeptide consisting of amino acids −19 to 396 of SEQ ID NO:2;
   (b) a polypeptide consisting of amino acids 1 to 396 of sequence of SEQ ID NO:2;
   (c) a polypeptide consisting of the full-length EDF polypeptide encoded by the human cDNA in ATCC™ Deposit No. 97407;
   (d) a polypeptide consisting of the mature form of the EDF polypeptide encoded by the human cDNA in ATCC™ Deposit No. 97407.

9. The isolated polypeptide of claim 8, wherein said polypeptide is (a).

10. The isolated polypeptide of claim 8, wherein said polypeptide is (b).

11. The isolated polypeptide of claim 8, wherein said polypeptide is (c).

12. The isolated polypeptide of claim 8, wherein said polypeptide is (d).

13. The isolated polypeptide of claim 8, wherein said polypeptide is glycosylated.

14. An isolated polypeptide comprising the polypeptide of claim 8, fused to a heterologous polypeptide.

15. An isolated polypeptide produced by a method comprising:
   (a) expressing the polypeptide of claim 8 by a cell; and
   (b) recovering said polypeptide.

16. An isolated polypeptide at least 95% identical to a polypeptide selected from the group consisting of:
   (a) a polypeptide comprising amino acids −19 to 396 of SEQ ID NO:2;
   (b) a polypeptide comprising amino acids 1 to 396 of sequence of SEQ ID No:2;
   (c) a polypeptide comprising the full-length EDF polypeptide encoded by the human cDNA in ATCC™ Deposit No. 97407;
   (d) a polypeptide comprising the mature form of the EDF polypeptide encoded by the human cDNA in ATCC™. Deposit No. 97407,
   wherein said polypeptide promotes bone formation or stimulates hematopoietic cell growth.

17. The isolated polypeptide of claim 16, wherein said polypeptide is (a).

18. The isolated polypeptide of claim 17, wherein said polypeptide consists of a polypeptide at least 95% identical to amino acids −19 to 396 of SEQ ID NO:2.

19. The isolated polypeptide of claim 16, wherein said polypeptide is (b).

20. The isolated polypeptide of claim 19, wherein said polypeptide consists of a polypeptide at least 95% identical to amino acids 1 to 396 of sequence of SEQ ID NO:2.

21. The isolated polypeptide of claim 16, wherein said polypeptide is (c).

22. The isolated polypeptide of claim 21, wherein said polypeptide consists of a polypeptide at least 95% identical to the full-length EDF polypeptide encoded by the human cDNA in ATCC™ Deposit No. 97407.

23. The isolated polypeptide of claim 16, wherein said polypeptide is (d).

24. The isolated polypeptide of claim 23, wherein said polypeptide consists of a polypeptide at least 95% identical to the mature form of the EDF polypeptide encoded by the human cDNA in ATCC™ Deposit No. 97407.

25. The isolated polypeptide of claim 16, wherein said polypeptide is glycosylated.

26. An isolated polypeptide comprising polypeptide (a), (b), (c), or (d) of claim 16, fused to a heterologous polypeptide.

27. An isolated polypeptide produced by a method comprising:
   (a) expressing the polypeptide of claim 16 by a cell; and
   (b) recovering said polypeptide.

* * * * *